(12) United States Patent
Paul et al.

(10) Patent No.: US 8,614,062 B1
(45) Date of Patent: Dec. 24, 2013

(54) RNA-BASED SYSTEM AND METHOD TO DIFFERENTIATE SEAFOOD

(75) Inventors: John H. Paul, Saint Petersburg, FL (US); David E. John, Clearwater, FL (US)

(73) Assignee: University of South Florida, Tampa, FL (US)

( * ) Notice: Subject to any disclaimer, the term of this patent is extended or adjusted under 35 U.S.C. 154(b) by 181 days.

(21) Appl. No.: 12/843,517

(22) Filed: Jul. 26, 2010

Related U.S. Application Data

(60) Provisional application No. 61/228,378, filed on Jul. 24, 2009.

(51) Int. Cl.
*C12Q 1/68* (2006.01)
*C07H 21/04* (2006.01)

(52) U.S. Cl.
USPC ......... 435/6.12; 435/6.1; 435/6.11; 536/24.3; 536/24.31

(58) Field of Classification Search
None
See application file for complete search history.

(56) References Cited

U.S. PATENT DOCUMENTS

| | | | |
|---|---|---|---|
| 4,851,330 A | 7/1989 | Kohne | |
| 5,409,818 A | 4/1995 | Davey et al. | |
| 5,853,981 A | 12/1998 | Kondo et al. | |
| 5,866,336 A | 2/1999 | Nazarenko et al. | |
| 6,218,531 B1 * | 4/2001 | Ekenberg | 536/25.41 |
| 6,355,421 B1 | 3/2002 | Coull et al. | |
| 2005/0158720 A1 | 7/2005 | Li et al. | |

FOREIGN PATENT DOCUMENTS

| | | |
|---|---|---|
| EP | 0329822 A2 | 8/1989 |
| WO | 9102818 A1 | 3/1991 |

OTHER PUBLICATIONS

Rodgers et al. Endocrinology. 2001, 142, 1412-1418.*
Genbank Accession No. AY731176.1 (Sep. 1, 2005).*
Buck et al. Biotechniques. (1999) 27(3):528-536.*
Bardakci et al., Application of the RAPD Technique in Tilapia Fish: Species and Subspecies Identification, Heredity, 1994, vol. 73, pp. 117-123.
Asensio et al., PCR-SSCP: A Simple Method for the Authentication of Grouper (*Epinephelus guaza*), Wreck Fish (*Polyprion americanus*), and Nile Perch (*Lates niloticus*) Fillets, J. Agric. Food Chem., 2001, vol. 49, pp. 1720-1723.
Casper et al., A Handheld NASBA Analyzer for the Field Detection and Quantification of Karenia Brevis, Harmful Algae, 2007, vol. 6, pp. 112-118.
Patterson et al., Increased Precision of Microbial RNA Quantification Using NASBA with an Internal Control, Journal of Microbiological Methods, 2005, vol. 60, pp. 343-352.
Farmer et al., Hand-Held Thermal-Regulating Fluorometer, Review of Scientific Instruments, 2005, vol. 76, pp. 115102-1-115102-5.

(Continued)

*Primary Examiner* — Stephen Kapushoc
*Assistant Examiner* — Joseph G Dauner
(74) *Attorney, Agent, or Firm* — Robert J. Varkonyi; Smith & Hopen, P.A.

(57) ABSTRACT

Substituting fish of lesser value for high priced fish such as grouper has become a major problem for restaurants, wholelsalers, and the general public. A method based upon nucleic acid amplification enables clear differentiation between grouper and potential substitutes. The nucleic acid is incubated with a molecular beacon probe thereby allowing detection of the hybridized molecular beacon probe. All grouper, including the fresh market sample, were successfully confirmed as grouper. Several non-grouper samples obtained fresh and frozen from the market were also tested; none were detected as grouper.

14 Claims, 10 Drawing Sheets

(56) References Cited

OTHER PUBLICATIONS

Tomalin, Grouper Regulations Bring Confusion, St. Petersburg Times, FL, Jan. 9, 2009, pp. C8.
Raghow, Regulation of Messenger RNA Turnover in Eukaryotes, TIBS, 1987, vol. 12, pp. 358-360.
Ishikawa et al., Comparative Studies on the Thermal Stability of Animal Ribosomal RNA's-VI. The 28S Ribosomal RNA of *Rhodnius prolixus* is Heat-Dissociable Only After its Purification, Comp. Biochem. Physiol., 1981, vol. 68B, pp. 377-381.
Scheler et al. 2011. "Detection of NASBA Amplified Bacterial tmRNA Molecules on SLICSel Designed Microarray Probes." BMC Biotechnology. vol. 11. No. 17. pp. 1-7.
Wikipedia. 2011. "Polymerase Chain Reaction." Wikimedia Foundation, Inc. Accessed Apr. 25, 2011.
Wikipedia. 2011. "NASBA (Molecular Biology)." Wikimedia Foundation, Inc. Accessed Apr. 25, 2011.
Patterson et al., A Nucleic Acid Sequence-Based Amplification Assay for Real-Time Detection of Norovirus Genogroup II, Journal of Applied Microbiology, 2006, vol. 101, pp. 956-963.
Baeumner et al., A Rapid Biosensor for Viable B. Anthracis Spores, Anal. Bioanal. Chem., 2004, vol. 380, pp. 15-23.
Copes, Attorney General, Tampa Restaurants Reach Agreement Over Fish Substitutions, Office of the Attorney General of Florida, Released Mar. 9, 2007.
Copes, McCollum: Settlement Reached with National Food Distributor over Grouper Allegations, Office of The Attorney General of Florida, Released Sep. 3, 2008.
Behlke et al., Fluorescence and Fluorescence Applications, Integrated DNA Technologies, 2005, pp. 1-13.
Frahm et al., Application of the Fluorogenic Probe Technique (TaqMan PCR) to the Detection of *Enterococcus* spp. and *Escherichia coli* in Water Samples, Journal of Microbiological Methods, 2003, vol. 52, pp. 123-131.
Haugland et al., Comparison of *Enterococcus* Measurements in Freshwater at Two Recreational Beaches by Quantitative Polymerase Chain Reaction and Membrane Filter Culture Analysis, Water Research, 2005, vol. 39, pp. 559-568.
He et al., Quantification of Enterococci and Human Adenoviruses in Environmental Samples by Real-Time PCR, Applied and Environmental Microbiology, 2005, vol. 71, No. 5, pp. 2250-2255.
Loens et al., Development of Conventional and Real-Time NASBA(R) for the Detection of *Legionella* Species in Respiratory Specimens, Journal of Microbiological Methods, 2006, vol. 67, pp. 408-415.
McElroy, Department Press Release: Bronson Announces Discovery of Nearly 8,000 Pounds of Bogus Grouper, FL Department of Agriculture and Consumer Services, Released May 9, 2006.
Van Der Wolf et al., Specific Detection of *Ralstonia solanacearum* 16S rRNA Sequences by AmpliDet RNA, European Journal of Plant Pathology, 2004, vol. 110, pp. 25-33.
Weusten et al., Principles of Quantitation of Viral Loads Using Nucleic Acid Sequence-Based Amplification in Combination with Homogeneous Detection Using Molecular Beacons, Nucleic Acids Research, 2002, vol. 30, No. 6, pp. 1-7.
Asensio et al., PCR-Based Methodology for the Authentication of Grouper (*Epinephelus marginatus*) in Commercial Fish Fillets, Food Control, 2008, pp. 1-5.
Yancy et al., Potential Use of DNA Barcodes in Regulatory Science: Applications of the Regulatory Fish Encyclopedia, Journal of Food Protection, 2008, vol. 71, No. 1, pp. 210-217.
Trotta et al., Multiplex PCR Method for Use in Real-Time PCR for Identification of Fish Fillets from Grouper (*Epinephelus* and *Mycteroperca* Species) and Common Substitute Species, Journal of Agricultural and Food Chemistry, 2005, vol. 53, pp. 2039-2045.
Espineira et al., Authentication of Anglerfish Species (*Lophius* spp) by Means of Polymerase Chain Reaction-Restriction Fragment Length Polymorphism (PCR-RFLP) and Forensically Informative Nucleotide Sequencing (FINS) Methodologies, Journal of Agricultural and Food Chemistry, 2008, vol. 56, pp. 10594-10599.
Ortea et al., Closely Related Shrimp Species Identification by MALDI-ToF Mass Spectrometry, Journal of Aquatic Food Product Technology, 2009, vol. 18, pp. 146-155.
Wen et al., The Application of PCR-RFLP and FINS for Species Identification Used in Sea Cucumbers (*Aspidochirotida: Stichopodidae*) Products from the Market, Food Control, 2010, vol. 21, pp. 403-407.
Aguilera-Munoz et al., Authentication of Commercial Chilean Mollusks Using Ribosomal Internal Transcribed Spacer (ITS) as Specie-Specific DNA Marker, Gayana, 2008, vol. 72, No. 2, pp. 178-187.
Espineira et al., Development of a Method for the Identification of Scombroid and Common Substitute Species in Seafood Products by FINS, Food Chemistry, 2009, vol. 117, pp. 698-704.
http://www.accessdata.fda.gov/scripts/SEARCH_SEAFOOD/index, accessed Aug. 23, 2010.
Casper et al., Detection and Quantification of the Red Tide Dinoflagellate Karenia Brevis by Real-Time Nucleic Acid Sequence-Based Amplification, Applied and Environmental Microbiology, 2004, vol. 70, No. 8, pp. 4727-4732.
Nohlgren, Payment Ends Inquiry Into Bogus Grouper, St Petersburg Times, FL, Sep. 4, 2008, pp. A1.
Nohlgren, State Finds More Grouper Imposters, St. Petersburg Times, FL, Jan. 30, 2007, pp. A1.
Rasmussen et al., DNA-Based Methods for the Identification of Commercial Fish and Seafood Species, Comprehensive Reviews in Food Science and Food Safety, 2008, vol. 7, pp. 280-295.
Ram et al., Authentication of Canned Tuna and Bonito by Sequence and Restriction Site Analysis of Polymerase Chain Reaction Products of Mitochondrial DNA, J. Agric. Food Chem., 1996, vol. 44, pp. 2460-2467.
Casper et al., Development and Evaluation of a Method to Detect and Quantify Enteroviruses Using NASBA and Internal Control RNA (IC-NASBA), Journal of Virological Methods, 2005, vol. 124, pp. 149-155.
Paul et al., In Situ Instrumentation, Oceanography, 2007, vol. 20, No. 2, pp. 70-78.

\* cited by examiner

Preliminary Molecular Beacon homology to target and non-target sequences

\* = 0-1 mismatches     + = 2-3 mismatches

− = 4-5 mismatches     ♦ = 6 or more mismatches

| WT Signal | 1.070 |
|---|---|
| Signal Detected | Δ:0.071 |
| SC Signal: | 1.000 |
| Signal Detected | Δ:0.000 |

WT Signal 2.397
Signal Detected Δ:1.397
SC Signal: 1.000
Signal Detected Δ:0.000

WT Signal 2.450
Signal Detected Δ:1.450
SC Signal: 1.000
Signal Detected Δ:0.000

| WT Signal | 2.501 |
| Signal Detected | Δ:1.501 |
| SC Signal: | 1.000 |
| Signal Detected | Δ:0.000 |

| WT Signal | 1.095 |
| Signal Detected | Δ:0.095 |
| SC Signal: | 1.000 |
| Signal Detected | Δ:0.000 |

*WT Signal*                      2.506
Signal Detected            Δ:1.506
*SC Signal*:                  1.000
Signal Detected            Δ:0.000

*WT Signal*                      2.644
Signal Detected            Δ:1.645
*SC Signal*:                  1.000
Signal Detected            Δ:0.000

| WT Signal | 2.526 |
| Signal Detected | Δ:1.526 |
| SC Signal: | 1.000 |
| Signal Detected | Δ:0.000 |

| WT Signal | 2.539 |
| Signal Detected | Δ:1.540 |
| SC Signal: | 1.000 |
| Signal Detected | Δ:0.000 |

| | |
|---|---|
| *WT Signal* | 2.218 |
| Signal Detected | Δ:1.218 |
| *SC Signal:* | 1.000 |
| Signal Detected | Δ:0.000 |

| WT Signal | 2.314 |
| Signal Detected | Δ:1.314 |
| SC Signal: | 1.000 |
| Signal Detected | Δ:0.000 |

| WT Signal | 2.266 |
| Signal Detected | Δ:1.267 |
| SC Signal: | 1.000 |
| Signal Detected | Δ:0.000 |

SEQUENCE LISTING

<160> NUMBER OF SEQ ID NOS: 7

<210> SEQ ID NO 1
<211> LENGTH: 19
<212> TYPE: DNA
<213> ORGANISM: artificial
<220> FEATURE:

```
<223> OTHER INFORMATION: forward primer

<400> SEQUENCE: 1
atgtctttgg ttggggcga                                              19

<210> SEQ ID NO 2
<211> LENGTH: 45
<212> TYPE: DNA
<213> ORGANISM: artificial
<220> FEATURE:
<223> OTHER INFORMATION: reverse primer

<400> SEQUENCE: 2
aattctaata cgactcacta tagggaagag gagattgcgc tgtta                 45

<210> SEQ ID NO 3
<211> LENGTH: 29
<212> TYPE: DNA
<213> ORGANISM: artificial
<220> FEATURE:
<223> OTHER INFORMATION: body of molecular beacon

<400> SEQUENCE: 3
cgatcgcgca aggaccgaat gtacgatcg                                   29

<210> SEQ ID NO 4
<211> LENGTH: 20
<212> TYPE: DNA
<213> ORGANISM: artificial
<220> FEATURE:
<223> OTHER INFORMATION: forward primer

<400> SEQUENCE: 4
ccccgcaagg accgaatgta                                             20

<210> SEQ ID NO 5
<211> LENGTH: 48
<212> TYPE: DNA
<213> ORGANISM: artificial
<220> FEATURE:
<223> OTHER INFORMATION: reverse primer

<400> SEQUENCE: 5
aattctaata cgactcacta tagggagaaa gaggagattg cgctgtta              48

<210> SEQ ID NO 6
<211> LENGTH: 32
<212> TYPE: DNA
<213> ORGANISM: artificial
<220> FEATURE:
<223> OTHER INFORMATION: body of molecular beacon

<400> SEQUENCE: 6
cgatgccatt cacaaccaag agcgacgcat cg                               32

<210> SEQ ID NO 7
<211> LENGTH: 32
<212> TYPE: DNA
<213> ORGANISM: artificial
<220> FEATURE:
<223> OTHER INFORMATION: body of molecular beacon

<400> SEQUENCE: 7
cgatcgcgtt tacaaccaag agctaccgat cg                               32
```

RNA-BASED SYSTEM AND METHOD TO DIFFERENTIATE SEAFOOD

CROSS REFERENCE TO RELATED APPLICATION

This application claims priority to U.S. Provisional Patent Application No. 61/228,378, entitled "Method to Differentiate Grouper Meat", filed on Jul. 24, 2009, the contents of which are herein incorporated by reference.

FIELD OF INVENTION

This invention relates to nucleic acid assays. Specifically, the invention provides a method of detecting the species classification of meat based on nucleic acids.

BACKGROUND OF THE INVENTION

A major challenge facing the seafood industry is confirming the identity of fish sold in restaurants, seafood markets, and by wholesalers. Mislabeling of seafood products, such as substituting more valuable species with less valuable ones, is a growing problem. (Trotta, et al.; Multiplex PCR methods for use in real-time PCR for identification of fish fillets from grouper (*Epinephelus* and *Mycteroperca* species) and common substitute species. J Agric Food Chem. 2005; 53: 2039-2045; Espiñeira, et al., Authentication of anglerfish species (*Lophius* spp) by means of polyermase chain reaction-restriction fragment length polymorphism (PCR-RFLP) and forensically informative nucleotide sequencing (FINS) methodologies. J Agric Food Chem. 2008; 56: 10594-10599; Wen, et al., The application of PCR-RFLP and FINS for species identification used in sea cucumbers (Aspidochirotide: Stichopodidae) products from the market. Food Control. 2010 April; 21(4):403-407; Ortea, et al., Closely related shrimp species identification by MALDI-ToF mass spectrometry. J Aquatic Food Prod Technol. 2009; 18: 146-155; Espiñeira, et al., Development of a method for the identification of scombroid and common substitute species in seafood products by FINS. Food Chem. 2009; 117: 698-704). A recent study found that as much as 77% of red snapper samples were mislabeled (Trotta, et al.; Multiplex PCR methods for use in real-time PCR for identification of fish fillets from grouper (*Epinephelus* and *Mycteroperca* species) and common substitute species. J Agric Food Chem. 2005; 53: 2039-2045).

Grouper species from the *Epinephelus* and *Mycteroperca* genera are in heavy demand (Trotta, et al.; Multiplex PCR methods for use in real-time PCR for identification of fish fillets from grouper (*Epinephelus* and *Mycteroperca* species) and common substitute species. J Agric Food Chem. 2005; 53: 2039-2045). Due to such high demand, sporadic availability, and therefore cost, grouper is commonly substituted with Nile perch (*Lates niloticus*) and wreck fish (*Polyprio americanus*) (Trotta, et al.; Multiplex PCR methods for use in real-time PCR for identification of fish fillets from grouper (*Epinephelus* and *Mycteroperca* species) and common substitute species. J Agric Food Chem. 2005; 53: 2039-2045). In Florida, the Department of Agriculture and Consumer Services has uncovered several instances of grouper substitution, including the discovery of almost 8,000 pounds of Vietnamese broadhead fillets marked for sale as grouper (McElroy, Department Press Release Bronson Announces Discovery of Nearly 8,000 Pounds Of Bogus Grouper. FL Department of Agriculture and Consumer Services. Released May 9, 2006). An investigation into grouper menu items in Tampa Bay area restaurants revealed substituted species to be emperor (generally a *Lethrinus* spp.), hake (typically *Urophycis* or *Merluccius* spp.), sutchi (*Pangasius hypophthalmus*), bream (numerous species are considered bream), green weakfish (*Cynoscion virescens*) and painted sweetlips (*Diagramma pictum*) (Copes, Attorney General Bill McCollum News Release: Attorney General, Tampa Restaurants Reach Agreement Over Fish Substitutions. Office of the Attorney General of Florida. Released Mar. 9, 2007), tilapia, bream, ponga, hake, and emperor fish as grouper "impostors" (Nohlgren, State finds more grouper impostors. St. Petersburg Times, St. Petersburg, Fla. Jan. 30, 2007, pg. A1).

Identification of seafood in the marketplace after the distinguishing external characteristics are removed (skin, fins, head, etc) is problematic; the flesh of many fish is similar enough that it can be difficult to identify the source (Wen, et al., The application of PCR-RFLP and FINS for species identification used in sea cucumbers (Aspidochirotide: Stichopodidae) products from the market. Food Control. 2010;:403-407; Espiñeira, et al., Development of a method for the identification of scombroid and common substitute species in seafood products by FINS. Food Chem. 2009; 117: 698-704; Aguilera-Muñoz, et al., Authentication of commercial chilean mollusks using ribosomal internal transcribed spacer (ITS) as specie-specific DNA marker. Gayana. 2008; 72(2): 178-187; Yancy, et al., Potential use of DNA barcodes in regulatory science: applications of the regulatory fish encyclopedia. J Food Protection. 2008; 71(1): 210-217).

In Florida, the Department of Agriculture and Consumer Services has uncovered several instances of grouper substitution, including the discovery of almost 8,000 pounds of Vietnamese broadhead fillets marked for sale as grouper (McElroy, Department Press Release: Bronson Announces Discovery of Nearly 8,000 Pounds Of Bogus Grouper. FL Department of Agriculture and Consumer Services Released. May 9, 2006). The Florida Attorney General's office has settled several complaints against restaurants and wholesalers. An investigation into grouper menu items in Tampa Bay area restaurants revealed substituted species to be emperor (generally a *Lethrinus* spp.), hake (typically *Urophycis* or *Merluccius* spp.), sutchi (*Pangasius hypophthalmus*), bream (numerous species are considered bream), green weakfish (*Cynoscion virescens*) and painted sweetlips (*Diagramma pictum*) (Copes, Attorney General Bill McCollum News Release: Attorney General, Tampa Restaurants Reach Agreement Over Fish Substitutions. Office of the Attorney General of Florida. Released Mar. 9, 2007). Additional media investigations have revealed tilapia, bream, ponga, hake, and emperor fish as grouper "impostors" (Nohlgren, State finds more grouper impostors. St. Petersburg Times, St. Petersburg, Fla. Jan. 30, 2007, pg. A1). Fines or settlements imposed to local restaurants and wholesale suppliers for intentionally or unintentionally serving or selling other fish for grouper are costly (Nohlgren, Payment ends inquiry into bogus grouper. St. Petersburg Times, St. Petersburg, Fla. Sep. 4, 2008, pg. A1); a recent settlement between the Florida Attorney General and a wholesaler in Florida was $300,000 (Copes, McCollum: Settlement Reached with National Food Distributor over Grouper Allegations. Office of the Attorney General of Florida. Released Sep. 3, 2008). Variable stocks and state and federal grouper catch regulations that are becoming more restrictive, and can be confusing (Tomalin, Changes bring confusion: As federal and state agencies tweak grouper regulations, recreational anglers scratch heads over rules and reasons. St. Petersburg Times, St. Petersburg, Fla. Jan. 9, 2009, pg. C8), may lead to more attempts at substitution of other fish products for grouper. Identification of the fish in the marketplace after the distinguishing external characteristics are removed (skin, fins, head, etc) is problematic; the flesh of many fish is similar enough that it can be difficult to identify the source. Various protein-based techniques including electrophoretic, immunologic, and chromatographic methods have been employed to identify fish fillets. The immunologic methods are best suited for analyzing large numbers of samples, whereas electrophoretic and chromatographic methods are complex and require facilities and instrumentation often not routinely available to seafood regulatory agencies (Rasmussen and Morrissey, DNA-Based methods for the identification of commercial fish and seafood species. Comprehensive Reviews in Food Science and Food Safety. 2008; 7: 280-295). While protein isoelectric focusing has been the standard method in use by the U.S. Food and Drug Administration (FDA) in the past, current methods are focused on nucleic acid-based technology.

Biochemical assays are being developed to aid in the identification of various seafood species, with many relying on the 16S ribosomal RNA gene or cytochrome oxidase I (COI) gene (Wen, et al., The application of PCR-RFLP and FINS for species identification used in sea cucumbers (Aspidochirotide: Stichopodidae) products from the market. Food Control. 2010 April; 21(4):403-407; Ortea, et al., Closely related shrimp species identification by MALDI-ToF mass spectrometry. J Aquatic Food Prod Technol. 2009; 18: 146-155). Further, assays are moving toward DNA-based analyses over protein-based assays, due to less degeneration of the genetic code and the presence of non-coding regions (Espiñeira, et al., Development of a method for the identification of scombroid and common substitute species in seafood products by FINS. Food Chem. 2009; 117: 698-704), though protein-based assays still find acceptance (Ortea, et al., Closely related shrimp species identification by MALDI-ToF mass spectrometry. J Aquatic Food Prod Technol. 2009; 18: 146-155). DNA-based methods afford greater resolution and speed in identifying fish species than protein-based techniques (Rasmussen and Morrissey DNA-Based methods for the identification of commercial fish and seafood species. Comprehensive Reviews in Food Science and Food Safety. 2008; 7: 280-295). Methods incorporating the polymerase chain reaction (PCR) include random amplified polymorphic DNA (DNA-RAPD; Bardakci and Skibinski, Application of the Rapd Technique in Tilapia Fish—Species and Subspecies Identification. Heredity. 1994; 73: 117-123), PCR restriction length polymorphisms (PCR-RFLP; Ram, et al. Authentication of canned tuna and bonito by sequence and restriction site analysis of polymerase chain reaction products of mitochondrial DNA. Journal of Agricultural and Food Chemistry. 1996; 44: 2460-2467), and PCR-single strand conformational polymorphism (PCR-SCCP; Asensio et al., PCR-SSCP: A simple method for the authentication of grouper (*Epinephelus guaza*), wreck fish (*Polyprion americanus*), and Nile perch (*Lates niloticus*) fillets. Journal of Agricultural and Food Chemistry. 2001; 49: 1720-1723). In all these methodologies, DNA is extracted from the tissue sample and purified. The PCR reaction is performed in a thermal cycler, and the resulting amplified DNA is then processed in a variety of ways, such as agarose gel to confirm presence and size, digestion to form a pattern of fragments that can be analyzed (PCR-RFLP) and compared to databases, or DNA sequencing. Current methods of identifying grouper from non-grouper fish use nucleic acid assays, such as those described by Kondo, et al. (U.S. Pat. No. 5,853,981) and Nazarenko, et al. (U.S. Pat. No. 5,866,336).

The FDA is in partnership with the Consortium for the Barcode of Life (CBOL) on research and validation of DNA bar-coding methods. This involves PCR amplification of a specific genetic locus, typically the mitochondrial cytochrome c oxidase I gene (COI), sequencing, and comparison of sequence to a database of sequences from verified, or vouchered, specimens (Yancy, et al., Potential use of DNA barcodes in regulatory science: Applications of the Regulatory Fish Encyclopedia. Journal of Food Protection. 2008; 71: 210-217). A related group, the Fish Barcode of Life Initiative (FISH-BOL), is building the bar-code database of fish species. The intended use of this methodology is to amplify a standardized fragment of the COI gene producing a 648 nucleotide product that is then sequenced and the sequence submitted to an online search engine (BOLD Systems, Barcode of Life identification engine; Biodiversity Institute of Ontario, University of Guelph, Guelph, ON) which performs the comparison to known sequences and produces an identification or close approximation. DNA bar-coding methodology has advantages, such as the use of a standardized genetic locus for characterization and standardized laboratory procedures for its amplification. The method provides a confirmed identity or at least a good approximation depending on database coverage of the species.

DNA-based methods afford greater resolution in identifying fish but are generally not workable outside the biotechnology laboratory. Further, the DNA require PCR amplification followed by some type of electrophoresis step or sequencing to confirm species identity. The size and power requirements to amplify DNA are largely dictated by the need for rapid and accurate temperature cycling. Although research is ongoing, development of a field-portable and especially hand-held PCR thermal cycler is a very technically daunting challenge.

Beyond the amplification of target sequences, DNA sequencing is even more daunting in hardware, reagent, and expertise requirements. While almost all molecular biology labs have the capability and expertise to perform PCR, sequencing is typically outsourced to relatively fewer labs with this capability, increasing the cost and turn-around time for results. A portable DNA sequencing device would be an even greater technological challenge than a portable PCR thermal cycler. Multiplex PCR and Real Time PCR have also been recently reported as methods to differentiate grouper from common substitutes (Trotta, et al. Multiplex PCR method for use in real-time PCR for identification of fish fillets from grouper (*Epinephelus* and *Mycteroperca* species) and common substitute species. Journal of Agricultural and Food Chemistry. 2005; 53: 2039-2045). Real-time PCR involves a specific probe molecule that fluoresces upon amplification of the target sequence in PCR. This method requires expensive instrumentation in the form of a real-time thermal cycler, an even more cumbersome and costly device than a standard thermal cycler. For these reasons, molecular identification of seafood has remained the purview of expensive molecular biology labs and trained lab technicians. A method to allow rapid and relatively easy identification of grouper tissues (i.e. seafood fillets) that could be performed by a variety of individuals with moderate technical skill would enable much broader testing for forensic and food quality applications. Such testing could then be performed at inspection points, fish markets, and even conceivably by restaurateurs. This technology would also be immensely beneficial to biological research employing biopsy hooks for non-lethal sampling of fishable stocks.

An alternative molecular technique termed nucleic acid sequence based amplification (NASBA) is similar to PCR in terms of amplification of specific nucleic acid sequences via an enzymatic reaction (Davey and Malek EP 0329822; Davey, et al.; WO/1991/002818). NASBA differs from PCR in some key ways however. NASBA reactions are simple and quick, with the assays taking as little as about an hour including incubation (Baeummer, et al., A rapid biosensor for viable *B. anthracis* spores. Anal Bioanal Chem. 2004; 380: 15-23). The system is based on an isothermal amplification protocol (i.e. does not require temperature cycling) that simplifies the hardware requirements; the process does not require a thermostable DNA polymerase or a thermal cycler, and works on RNA rather than DNA. Work using NASBA as shown the system able to target and quantify a series of microbial RNAs in the marine environment (Casper et al. Detection and quantification of the red tide dinoflagellate *Karenia brevis* by real-time nucleic acid sequence-based amplification. Appl Environ Microbiol. 2004; 70: 4727-4732; Casper et al. Development and evaluation of a method to detect and quantify enteroviruses using NASBA and internal control RNA (IC-NASBA). J. Virol. Methods. 2005; 124: 149-155; Patterson, et al., A nucleic acid sequence-based amplification assay for real-time detection of norovirus genogroup II. J. Appl. Microbiol. 2006; 101: 956-963).

Thus, while DNA barcode amplification and sequencing will likely continue to be advanced as a conclusive tissue identification technique, the complexity of this procedure precludes use outside a molecular biology laboratory for the near future. However, with a simple yet robust sample preparation protocol and relatively simple device, a field-use NASBA detection procedure is very feasible for specific applications, such as confirmation of a particular seafood product.

SUMMARY OF THE INVENTION

A protocol was developed for the detection of a target seafood species, such as grouper, based or differentiation of grouper (as defined by the FDA) meat and/or tissue (fresh or frozen) from other fish meat based upon Nucleic Acid Sequence-Based Amplification (NASBA) amplification of target sequences specific for grouper. RNA is extracted from a sample of muscle from a fish and amplified using nucleic acid based amplification. Specific primer sequences and molecular beacons, were designed for the amplification and detection of target sequences in the mitochondria (16 S ribosomal RNA). The resulting product of the amplified RNA is indicative of positive detection of the target fish species. The assay may be analyzed by electrophoresis, laboratory instrumentation such as benchtop luminescence detection of a molecular beacon, or through use of a field NASBA analyzer like a handheld fluorescence detection device. In specific embodiments of the invention, the assay and hardware are simplified such that semi-skilled staff can successfully differentiate grouper from other fish in situ, such as at seafood markets, restaurants, and aboard ships (Paul, et al., In Situ Instrumentation. Oceanography. 2007; 20: 70-78).

The hardware and power requirements for NASBA are drastically simplified vs. PCR: all that is needed for NASBA and molecular beacon detection is a simple fluorometer with constant temperature control (41° C.).

Molecular beacons are hairpin-shaped oligonucleotides, as seen in FIG. 2. The stem of the beacon is formed by complementary sequences at both ends of the oligonucleotide. A fluorescent label and a quenching group are attached at the two ends of the molecule. In its unbound form, the stem holds the two groups close together, causing the fluorescence of the fluorophore to be quenched by energy transfer. When the molecular beacon encounters a target molecule, having a complementary sequence to the loop, the molecular beacon hybridizes to the target molecule, moving the quencher away from the fluorophore and allowing for a fluorescent signal (Weusten, et al. et al. Principles of quantitation of viral loads using nucleic acid sequence-based amplification in combination with homogeneous detection using molecular beacons. Nucleic Acids Res. 2002 Mar. 15; 30(6):e26).

Molecular probe or probes are optionally included in the nucleic acid based amplification, and designed to specifically bind to a region of the rRNA generating a fluorescence signal which correlates to positive binding of the molecular probe to a target sequence. In nucleic acid sequence-based amplification (NASBA) assay utilizing molecular beacons, the molecular beacons hybridize to single-stranded amplicons and provide an optical signal of amplification in real-time, much like real-time PCR. This allows for a comparison of the signal generated from hybridization of the molecular beacon to a control sequence against the signal generated from hybridization of the molecular beacon to the fish sample, to establish a ratio which is indicative of positive detection of the target fish species. In specific variations of the invention, positive detection of the target fish species is premised upon the fluorescence exceeding a threshold value ratio of 1.34 or 1.3 target signal to the baseline fluorescence.

In certain embodiments, a known amount of calibrator RNA is added concomitantly with the test sample, and serves as an internal control. NASBA signal amplification and molecular beacon binding produce a fluorescence signal which corresponds to the relative amount of amplicon in the reaction, permitting real-time detection during the amplification phase. Molecular probes designed for hybridization to the calibrator RNA and sequence of interest are added to the reaction. Because the calibrator RNA contains a unique sequence to the test RNA, sequence specific amplification and hybridization to a sequence-specific molecular probe occur. This provides two discrete signals concurrently, one for the calibrator RNA and one for the test RNA. Comparing the two fluorescent signals allows for quantitative determination of the test RNA.

Other optional molecular beacons include negative controls to detect for cross-reactivity. In such embodiments, an additional reaction tube, which if positive, will indicate a non-grouper species is detected. Thus, we can craft the negative detection assay(s) to include these and other common substitutes that are considered problematic.

Optional additional oligonucleotides (primers and beacons) are added to cover additional species and/or specifically detect undesired substitutes. The optional oligionucleotides and molecular beacons are multiplexed into combined reactions. Since identification of the individual species is not intended, confirmation as one of the grouper with a single positive reaction is possible. Such optional primers would also focus on the 16S rRNA, corresponding to the region disclosed herein. The design of such primers is within the skill of one working in the field, taking into consideration the disclosed rRNA regions disclosed.

The methods may be included as a kit for detecting whether seafood originates from a target fish species, which would include a muscle tissue extractor, such as a biopsy punch, an RNA extraction system adapted to accept a muscle tissue sample from the muscle tissue extractor, a nucleic acid based amplification reaction tube adapted to accept RNA from the RNA extraction system, and a fluorescence detection device adapted to accept the nucleic acid based amplification reaction tube and maintain a set temperature. The RNA extraction system provided in the kit optionally includes a lysis buffer, a RNA purification column having an input adapted to accept the lysis buffer and cellular debris and an output, at least one syringe adapted to fit on the input of the RNA purification column, at least one syringe filled with acetone or ethyl alcohol, and adapted to fit on the input of the RNA purification column, and at least one syringe filled with RNA elution solution, and adapted to fit on the input of the RNA purification column. The nucleic acid based amplification reaction tube includes as least a forward primer and a reverse primer for the nucleic acid based amplification which are designed to specifically amplify a region of 16S rRNA of a target fish species.

The kit optionally further comprising at least one molecular probe, where the at least one molecular prove is designed to specifically bind to a region of the rRNA generating a fluorescence signal which correlates to positive binding of the molecular probe to a target sequence. Additional molecular beacons are also optionally included to bind to and detect different species of fish from the target fish species, designed not to bind to any species of fish, designed to bind to a control sequence, or a combination thereof.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

NASBA assays were used to develop a field detection system to identify tissue from fish species classified as "grouper" on the US FDA Seafood List from potential substitutes. Advantageously, the system is suitable for field use with a portable handheld device. The system utilizes a handheld thermoregulated fluorometer to perform the NASBA amplification and detection of the amplified product with molecular beacons.

As used herein, "grouper" is a fish of Perciformes, Serranidae, subfamily Epinephelinae. Some exemplary species are found in the genera *Epinephelus, Mycteroperca* and *Cephalopholis*. The FDA currently recognizes 52 fish as grouper for seafood marketing (2008 FDA Seafood List). This listing includes 7 genera/species not falling under the genera *Epinephelus, Mycteroperca*, or *Cephalopholis*. These are *Variola louti, Caprodon schlegelii, Anyperodon leucogrammicus, Plectropomus leopardus, Plectropomus areolatus, Plectropomus* spp. (presumably any in this genus), and *Diplectrum formosum*.

As used herein, "muscle tissue" is contractile tissue of a fish. The term "meat" or "muscle" refers to the edible tissue of a fish.

As used herein, "molecular probe" is a molecule, such as a nucleic acid or non-nucleic acid polymer like DNA, RNA, PNA, nucleic acid analogs, nucleic acid mimics, chimera, or linked polymer, having a probing nucleobase sequence that is designed to specifically and differentially bind or hybridize to a target sequence of nucleic acid. The molecular probe is designed to bind or hybridize specifically to a target molecule and generate a detectable signal upon reacting with a nucleic acid target, with insignificant binding to non-target sequences, such that non-target sequences do not produce a detectable signal.

Figure 1:
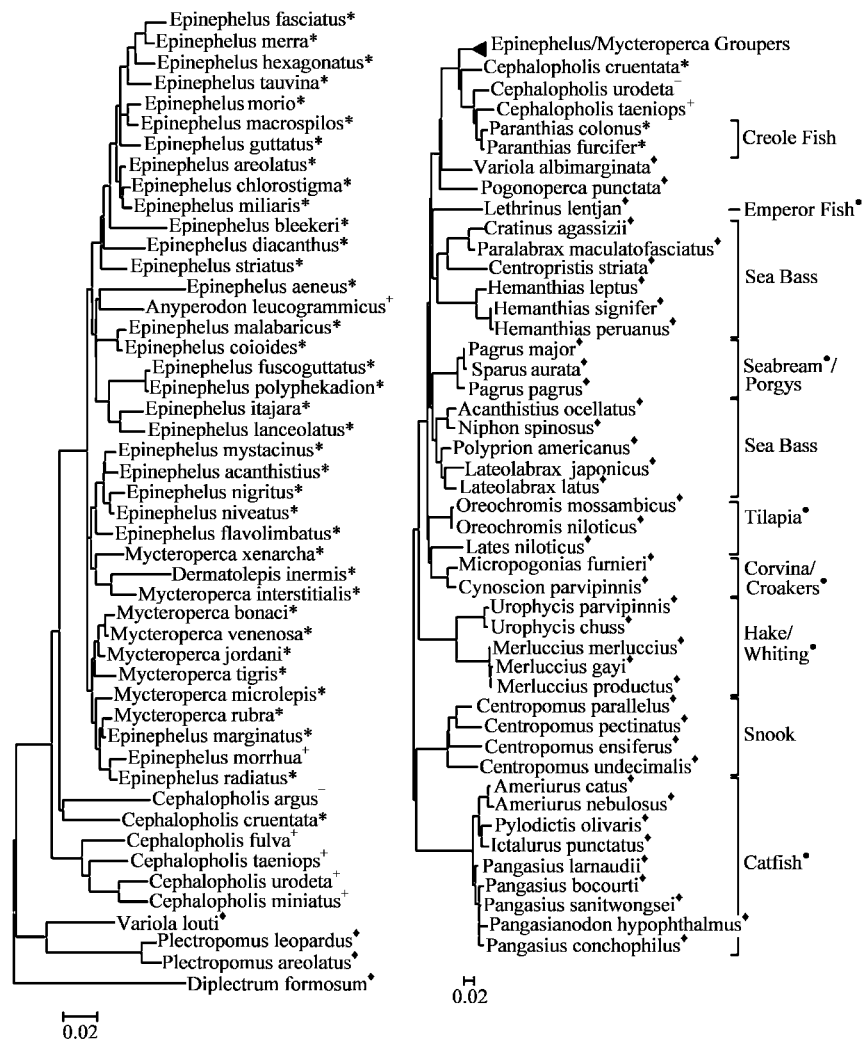
FIG. 1 is a diagram of phylogenetic trees reflecting mitochondrial 16S rRNA sequence from grouper and non-grouper species. Left: species with the market name grouper per US FDA 2008 Seafood List. Omitted is *Caprodon schlegelii* for which rRNA sequence information is not currently available. Right: non-target species, including some that have been discovered as misbranded grouper (*). Color-coding reflects number of mismatches to the molecular beacon in preliminary grouper NASBA assay. Members of the *Cephalopholis* are also considered grouper, although some of these species may not have commercial value as a grouper product.

As used herein, "frozen" means the solidification of material, such as the solidification of water into ice, and the storage of food materials in such solid state. For example, frozen tissue is cellular material which is in a solid state While most DNA bar-coding efforts currently target the mitochondrial COI gene, the grouper NASBA assay targets the mitochondrial 16S ribosomal RNA (rRNA). Since NASBA works by amplifying RNA (rather than DNA), targeting the rRNA is advantageous since rRNA is dramatically more stable in non-living cells than the messenger RNA (mRNA) that would have to be targeted if using the COI gene product (Ishikawa et al., Comparative studies on the thermal-stability of animal ribosomal-RNA. The 28S ribosomal-RNA of *Rhodnius-Prolixus* is heat-dissociable only after its purification. Comparative Biochemistry and Physiology B—Biochemistry & Molecular Biology. 1981; 68: 377-381; Raghow, Regulation of messenger-RNA turnover in eukaryotes. Trends Biochem. Sci. 1987; 12: 358-36). Research has indicated that rRNA inside animal cells is thermostable, and becomes heat-dissociable only after extraction from cells (Ishikawa et al., Comparative studies on the thermal-stability of animal ribosomal-RNA. The 28S ribosomal-RNA of *Rhodnius-Prolixus* is heat-dissociable only after its purification. Comparative Biochemistry and Physiology B—Biochemistry & Molecular Biology. 1981; 68: 377-381). Also, rRNA is much more prevalent in cells; about 95% of cellular RNA is composed of rRNA with mRNA making up <5%. There is also considerable sequence information available on fish rRNA via Genbank. FIG. 1 depicts phylogenetic trees of the mitochondrial 16S rRNA sequences from numerous grouper and non-grouper fish species, including many of those that have been misbranded as grouper in Florida. On both diagrams, the number of mismatches to the molecular beacon sequence is indicated. This enables evaluation of potential beacon sequences and their specificity using bioinformatics rather than blindly testing the many potential targets and non-targets for specificity.

A small (5-10 mg) piece of sample tissue, such as fish muscle tissue, was immersed in lysis buffer and soaked for 30 seconds to up to 10 minutes, with occasional agitation. The buffer, containing liberated RNA, was transferred to the purification column (Zymo Mini RNA isolation II kit, Zymo Research Corp., Orange, Calif.) and a syringe attached to the column to pressurize the column and force the lysis buffer liquid through the column. A series of buffers (Zymo Mini RNA isolation II kit), preloaded into syringes, were run through the column, followed by 100% acetone. It is noted that other agents, such as 100% ethyl alcohol made be used in place of the acetone. Finally, a volume of water was used to elute the RNA from the column and into a sample container.

The NASBA assay principally consists of upstream and downstream primers that facilitate the amplification reaction, and a molecular beacon to permit detection of the specific amplified sequence, with the beacon establishing target specificity (Weusten, et al. Principles of quantitation of viral loads using nucleic acid sequence-based amplification in combination with homogeneous detection using molecular beacons. Nucleic Acids Res. 2002 Mar. 15; 30(6):e26). The grouper NASBA assay targets the mitochondrial 16S ribosomal RNA (rRNA). NASBA was performed using the Nuclisens Basic Kit (bioMérieux, Durham, N.C., USA) and an EasyQ incubator and detection system (bioMérieux). The NASBA assay is an isothermal process that uses three enzymes (AMV-RT, RNase H and T7 RNA polymerase) and target-specific oligonucleotides, shown below, to generate a single-stranded RNA product. All water used was nuclease-free water, unless noted otherwise. Primers were diluted to 1:4 concentrations of 100 µM. The molecular beacon was labeled with 6-carboxy fluorescein (6-FAM) at its 5'-end and quencher Dabcyl at its 3'-end, illustrated in FIG. 2. The molecular beacon was diluted at 100 µM stock concentration 1:4.16. A primer mix was made using 4 µl each diluted primer, 1 µl diluted beacon, and 1 µl water. To a reagent tube, 80 µl reagent diluent, 16 µl KCl stock, and 14 µl water, were mixed and added to reagent. The pre-made primer mix was added to the reagent tube, followed by 55 µl enzyme diluent. For each reaction, 5 µl reagent mix, and 2.5 µl purified RNA were mixed, and heated at 65° C. for 2 minutes. To the reaction, 2.5 µl enzyme was added, and the reaction placed in a fluorescence reader at 41° C. to analyze. This allowed hybridization of the target nucleic acid and molecular probe. The product is detected with a dedicated fluorescent reader, which reads fluorescence from reaction tubes using direct and focused illumination. Specific filters are used for both excitation and emission of the molecular beacons in the assays. The filters are automatically selected by the requested assay protocol.

TABLE 1

Primer and Molecular Beacons.

| SEQ ID | Oligo Name | Sequence |
|---|---|---|
| SEQ ID NO: 1 | Forward Primer 1 | ATG TCT TTG GTT GGG GCG A |
| SEQ ID NO: 2 | Reverse Primer 1 | AAT TCT AAT ACG ACT CAC TAT AGG GAA GAG GAG ATT GCG CTG TTA |

TABLE 1-continued

Primer and Molecular Beacons.

| SEQ ID Oligo Name | Sequence |
|---|---|
| SEQ ID NO: 3 Mol Beacon 1 | [6-FAM]CGA TCG CGC AAG GAC CGA ATG TAC GAT CG[Dabcyl] |
| SEQ ID NO: 4 Forward Primer 2 | CCC CGC AAG GAC CGA ATG TA |
| SEQ ID NO: 5 Reverse Primer 1 | AAT TCT AAT ACG ACT CAC TAT AGG GAG AAA GAG GAG ATT GCG CTG TTA |
| SEQ ID NO: 6 Mol Beacon 2 | [6-FAM]CGA TGC CAT TCA CAA CCA AGA GCG ACG CAT CG[Dabcyl-Q] |
| SEQ ID NO: 7 Mol Beacon 3 | [6-FAM]CGA TCG CGT TTA CAA CCA AGA GCT ACC GAT CG[Dabcyl-Q] |

Fluorescence data was collected from the EasyQ analyzer and processed by a custom Microsoft Excel-based software for real time data plotting. Fluorescence curves are generated for the target amplification and, where appropriate, another is generated for the internal control amplification. The raw numeric data is stored in an Excel worksheet-compatible format.

Example 1

A grouper-specific NASBA fluorometric assay was designed to detect grouper, such as members of the genera *Epinephelus* and *Mycteroperca* and some of *Cephalopholis*. RNA was extracted from fish tissue using minute quantities of fish tissue samples, as discussed above. Briefly, sample tissue (5-10 mg) was immersed in 1.0 ml lysis buffer for up to 10 minutes with occasional agitation. It is noted that the amount of lysis buffer may be increased or decreased. For example, 0.8 ml, 0.9 ml, 1.1 ml, or 1.2 ml may be used. The resulting buffer was transferred to a purification column and RNA extracted (Zymo Mini RNA isolation II kit), which involves two buffers and a purification column. The manufacturer's protocol was followed to wash and complete RNA extraction.

Figure 2:
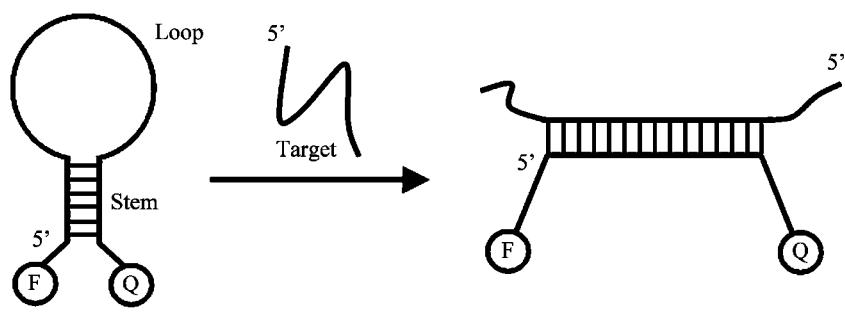
FIG. 2 is an illustration of the molecular probe hybridization to target RNA and generation of a fluorescent signal.
Figure 3:
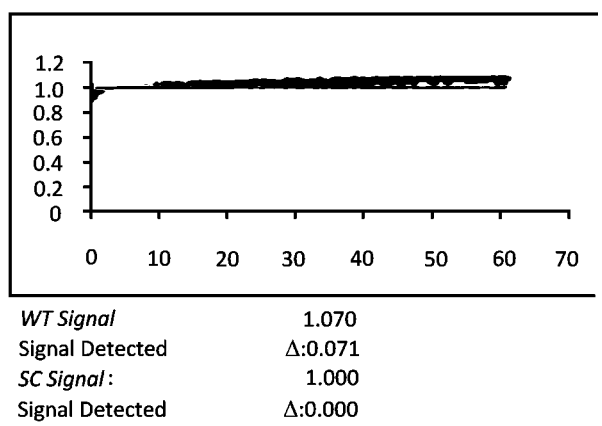
FIG. 3 is a graph showing negative controls from NASBA amplification procedures. The black line reflects fluorescence of the reporter molecule from the beacon (Beacon SEQ ID NO: 6 only).
Figure 4:
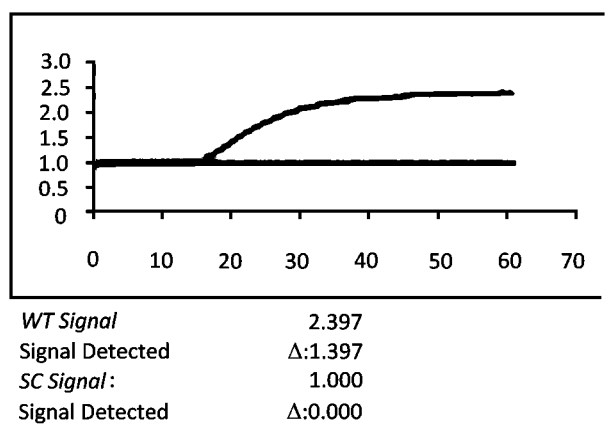
FIG. 4 is a graph showing NASBA amplification of RNA from grouper tissue of *Epinephelus diacanthus* 1. The black line reflects fluorescence of the reporter molecule from the beacon (Beacon SEQ ID NO: 6 only). The sharp increase and sigmoidal shape indicate a positive detection.
Figure 5:
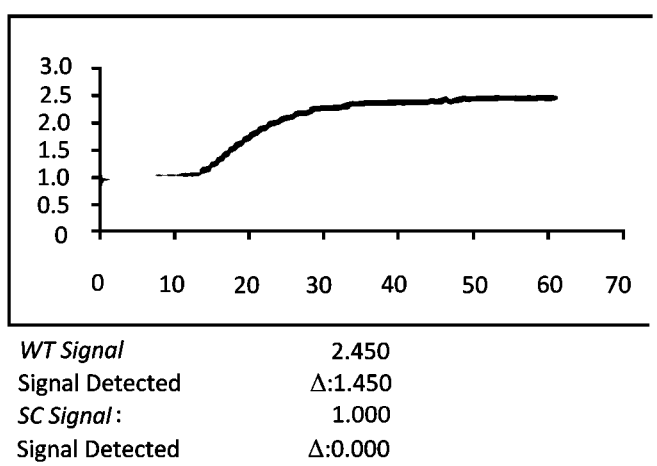
FIG. 5 is a graph showing NASBA amplification of RNA from grouper tissue of *Epinephelus diacanthus* 2. The black line reflects fluorescence of the reporter molecule from the beacon (Beacon SEQ ID NO: 6 only). The sharp increase and sigmoidal shape indicate a positive detection.
Figure 6:
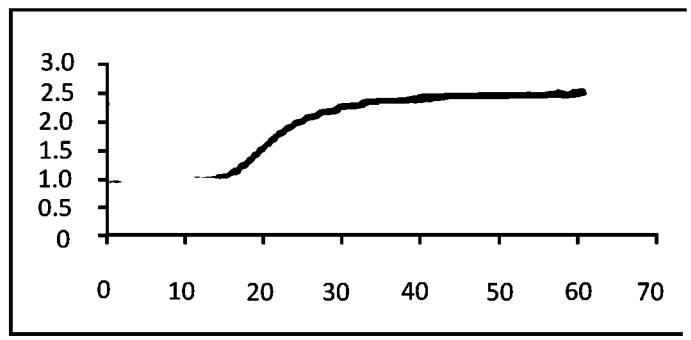
FIG. 6 is a graph showing NASBA amplification of RNA from grouper tissue of *Epinephelus morio*. The black line reflects fluorescence of the reporter molecule from the beacon (Beacon SEQ ID NO: 6 only). The sharp increase and sigmoidal shape indicate a positive detection.
Figure 7:
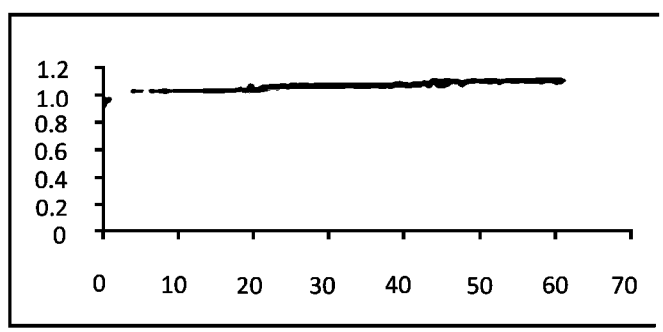
FIG. 7 is a graph showing negative controls from NASBA amplification procedures. The black line reflects fluorescence of the reporter molecule from the beacon (Beacon SEQ ID NO: 6 only). The sharp increase and sigmoidal shape indicate a positive detection.
Figure 8:
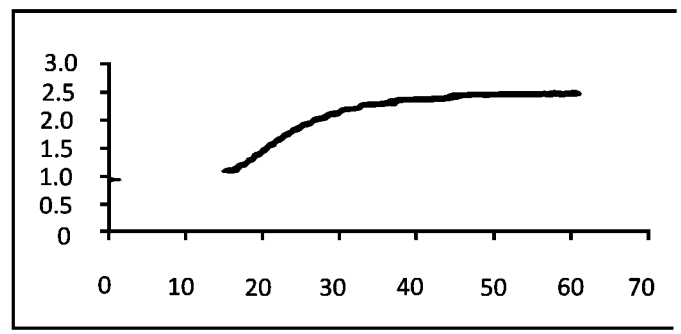
FIG. 8 is a graph showing NASBA amplification of RNA from grouper tissue of *Epinephelus diacanthus* 1. The black line reflects fluorescence of the reporter molecule from the beacon (Beacon SEQ ID NO: 1 only). The sharp increase and sigmoidal shape indicate a positive detection.
Figure 9:
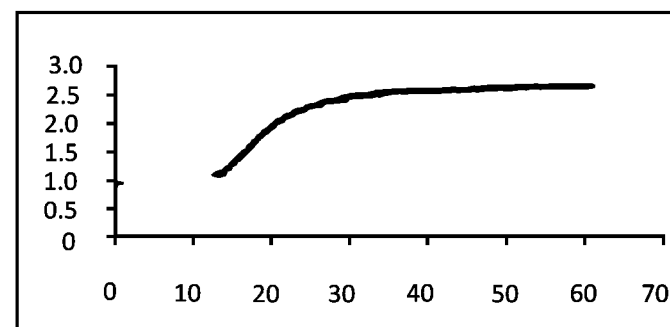
FIG. 9 is a graph showing NASBA amplification of RNA from grouper tissue of *Epinephelus diacanthus* 2. The black line reflects fluorescence of the reporter molecule from the beacon (Beacon SEQ ID NO: 1 only). The sharp increase and sigmoidal shape indicate a positive detection.
Figure 10:
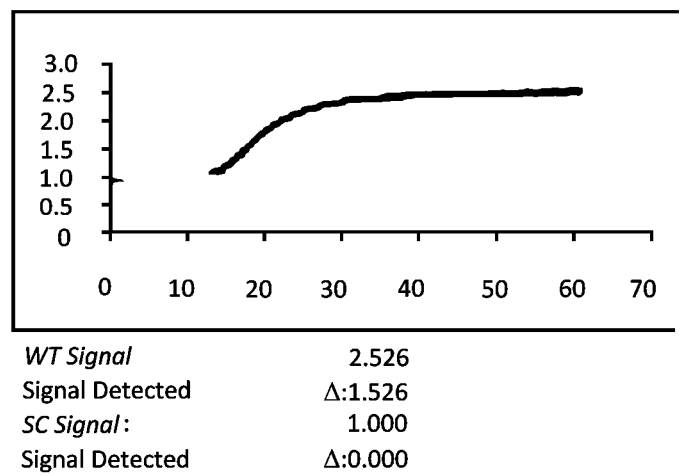
FIG. 10 is a graph showing NASBA amplification of RNA from grouper tissue of *Mycteroperca microlepis*. The black line reflects fluorescence of the reporter molecule from the beacon (Beacon SEQ ID NO: 1 only). The sharp increase and sigmoidal shape indicate a positive detection.
Figure 11:
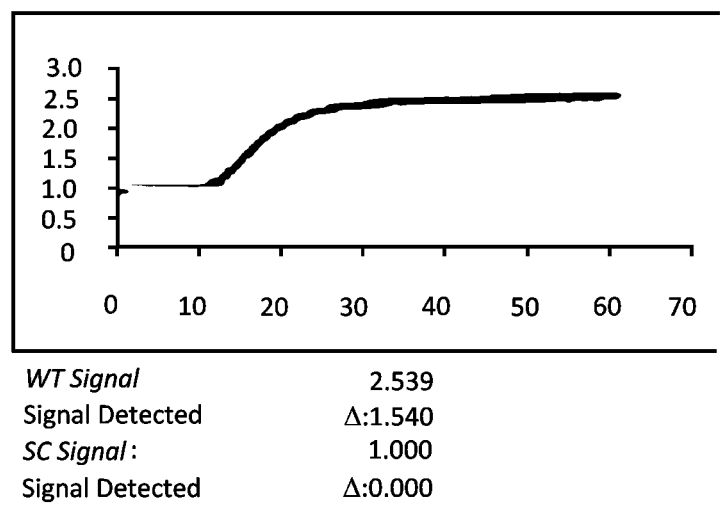
FIG. 11 is a graph showing NASBA amplification of RNA from grouper tissue of an in-vitro transcript from *Mycteroperca microlepis* cloned gene. The black line reflects fluorescence of the reporter molecule from the beacon (Beacon SEQ ID NO: 1 only). The sharp increase and sigmoidal shape indicate a positive detection.

Extracted RNA samples were run using the Nuclisens NASBA reagent, with all dilutions in nuclease-free water unless noted otherwise, and all water nuclease-free. Primers and a molecular beacon were designed to specifically detect the large majority of grouper species using rRNA. Additional beacons are optionally added to further enhance detection and differentiation of the species. The grouper NASBA assay targets the mitochondrial 16S ribosomal RNA (rRNA). Note that this does not target DNA, but the specific sequences are derived from the gene sequences coded by the DNA. The molecular beacon was diluted at 100 µM stock concentration 1:4.16 and primers at 100 µM concentration 1:4. A primer mix was made using 4 µl each diluted primer, 1 µl diluted beacon, and 1 µl water. To a reagent tube, 80 µl reagent diluent, 16 µl KCl stock, and 14 µl water, were mixed and added to reagent. The pre-made primer mix was added to the reagent tube, followed by 55 µl enzyme diluent. For each reaction, 5 µl reagent mix, and 2.5 µl purified RNA were mixed, and heated at 65° C. for 2 minutes. To the reaction, 2.5 µl enzyme was added, and the reaction placed in EasyQ (bioMérieux, Durham, N.C., USA) reader at 41° C. to analyze. This allowed hybridization of the target nucleic acid and molecular probe, as seen in FIG. 2. The amplified RNA was analyzed contemporaneously with the NASBA reaction using an EasyQ NASBA reader. The NASBA assay oligonucleotides are as follows:

Forward primer: ATG TCT TTG GTT GGG GCG A (SEQ ID NO: 1).
Reverse primer: AAT TCT AAT ACG ACT CAC TAT AGG GAA GAG GAG ATT GCG CTG TTA (SEQ ID NO: 2).

Molecular beacons are a novel class of DNA hybridization probes, with a stem-loop structure, a fluorophore, and a quencher group, seen in FIG. 2. In its normal state the stem keeps the fluorophore and the quencher together, preventing emission or fluorescence. In the presence of a sequence complementary to the loop sequence, the probe unfolds and hybridizes, preventing the quencher from absorbing photons emitted by the fluorophore, and the probe starts to fluoresce. The beacon establishes target specificity, and is labeled with the fluorophores 6-FAM on the 5' end and Dabcyl on the 3' end, although other fluorophores and quenchers can replace these.

Molecular Beacon: '5 6-FAM/CGA TCG CGC AAG GAC CGA ATG TAC GAT CG/3' Dabcyl (SEQ ID NO: 3).

This assay has been tested on numerous samples from gag and red grouper, along with several non-grouper seafood products. FIG. 1 depicts phylogenetic trees of the mitochondrial 16S rRNA sequences from numerous grouper and non-grouper fish species. On both diagrams, the number of mismatches to the molecular beacon sequence are indicated. Based on prior experiences, beacons with three or more mismatches fail to detect the target.

Additional grouper samples included that from a gag stored frozen at ~−20° C. for several years provided by David Mann of USF, and a sample from a grouper fillet sold fresh at a local market. Numerous samples from gag and red grouper were collected with the assistance of Chris Koenig at Florida State University as live caught fish; tissue samples were obtained via biopsy punches and stored in RNA preservative (RNALater) at −20° C. Table 2 summarizes the test results. All grouper, including the fresh market sample, were successfully confirmed as grouper. Several non-grouper samples obtained fresh and frozen from the market were also tested; none were detected as grouper.

TABLE 2

Results of preliminary testing using Grouper NASBA assay.

| Fish | Storage | Source | Time to positivity (minutes) | st. dev. |
|---|---|---|---|---|
| Gag (16 individuals) | frozen | GoM live caught | 29.3 (average) | 3.8 |
| Red Grouper (8 indiv.) | frozen | GoM live caught | 29.6 (average) | 4.6 |

TABLE 2-continued

Results of preliminary testing using Grouper NASBA assay.

| Fish | Storage | Source | Time to positivity (minutes) | st. dev. |
|---|---|---|---|---|
| Gag (1) | frozen | unknown | 28.5 | |
| Grouper, sp. unknown (1) | fresh | market | 30.0 | |
| Catfish (1) | fresh | market | NA | |
| Flounder (1) | frozen | market | NA | |
| Haddock (1) | frozen | market | NA | |
| mahi-mahi (1) | frozen | market | NA | |
| Tilapia (1) | fresh | market | NA | |
| Triggerfish (1) | frozen | unknown | NA | |

A total of 25 grouper tissue samples were analyzed, and 6 different non-grouper samples. The market-fresh grouper was not identified to species level. These results also demonstrate the stability of the rRNA molecular target under a variety of storage conditions.

Additional grouper assessment for performance evaluation was based upon time to positivity measurements, seen in Table 2. This is the time from start of reaction until fluorescence crosses a threshold. Typically for assays run on the EasyQ, this is a ratio of 1.34 to the baseline fluorescence. Time to positivity is thus a quantitative measure of the efficiency of the reaction, and a useful guide to determine the effect of a changed parameter. Reactions that do not reach the designated fluorescence threshold are considered negative. Testing showed that the reaction reaches confirmed positivity in about 25-30 minutes.

Example 2

Additional primer sequences and molecular beacons were designed (Eurofins MWG Operon, Ebersberg, Germany), with an upstream primer sequence lying on part of the 16S rRNA gene that was occupied by the original beacon. This permits the phylogenetic specificity against non-target fish species from Example 2. New beacons were designed with enhanced folding of the single-stranded DNA molecule.

The new oligonucleotides were tested initially using RNA extracted from fish tissue samples by traditional RNA extraction using centrifugation (Zymo Mini RNA isolation II kit). Extracted RNA samples were run using the Nuclisens NASBA reagent, as discussed in Example 2. The molecular beacon was diluted at 100 µM stock concentration 1:4.16 and primers at 100 µM concentration 1:4. A primer mix was made using 4 µl each diluted primer, 1 µl diluted beacon, and 1 µl water. To a reagent tube, 80 µl reagent diluent, 16 µl KCl stock, and 14 µl water, were mixed and added to reagent. The pre-made primer mix was added to the reagent tube, followed by 55 µl enzyme diluent. The NASBA assay oligonucleotides are as follows:
Forward primer: CCC CGC AAG GAC CGA ATG TA (SEQ ID NO: 4).
Reverse primer: AAT TCT AAT ACG ACT CAC TAT AGG GAG AAA GAG GAG ATT GCG CTG TTA (SEQ ID NO: 5).

On the reverse primer, the first 25 nucleotides (underlined) represent the promoter sequence for T7 RNA polymerase. The last 20 nucleotides (bolded) are complementary to the 16S rRNA gene and composes the gene specific binding region.
Beacons:
5'-[6-FAM]CGA TGC CAT TCA CAA CCA AGA GCG ACG CAT CG[Dabcyl-Q]-3' (SEQ ID NO: 6).
5'-[6-FAM]CGA TCG CGT TTA CAA CCA AGA GCT ACC GAT CG[Dabcyl-Q]-3' (SEQ ID NO: 7).

On the beacons, the middle 20 nucleotides (7-26, bolded) are the gene specific binding region. The designations on the end indicate the reporter (FAM) and quencher (DABCYL) fluorophore molecules.

For each reaction, 5 µl reagent mix, and 2.5 µl purified RNA were mixed, and heated at 65° C. for 2 minutes. To the reaction, 2.5 µl enzyme was added, and the reaction placed in EasyQ reader at 41° C. to analyze.

The results for SEQ ID 6 are shown in FIGS. 3-11. The beacon is specific for most of the grouper species in the genera Epinephelus and Mycteroperca. The second beacon (SEQ ID NO: 7) is more specific to some of the hinds. As seen from FIGS. 4-5 and 8-11, a sharp, parabolic increase in the molecular probe signal is indicative of detection of grouper species.

Example 3

RNA extracted from fish tissue samples by traditional RNA extraction using centrifugation (Zymo Mini RNA isolation II kit) and the RNA run using the Nuclisens NASBA reagent, as discussed in Example 3. The NASBA reaction was then placed in a handheld detector unit (Bioplex SE-100, Bioplex Technologies, Inc., St. Petersburg, Fla.) at 41° C. to analyze.

Figure 12:
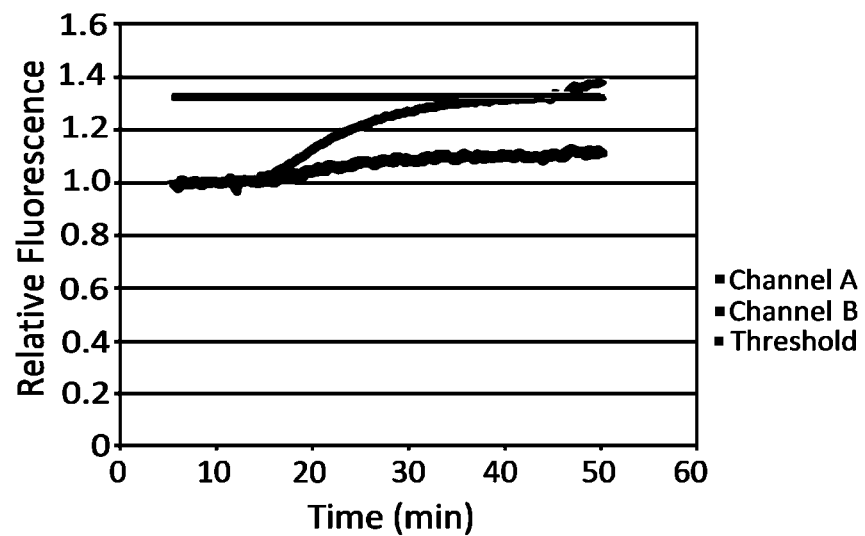
FIG. 12 is a graph showing results from NASBA analysis using the handheld detector for *Mycteroperca microlepis*. The flat light grey line indicates a ratio of 1.3 from the baseline (initial) fluorescence, a benchmark we typically use to indicate the reaction is positive.
Figure 13:
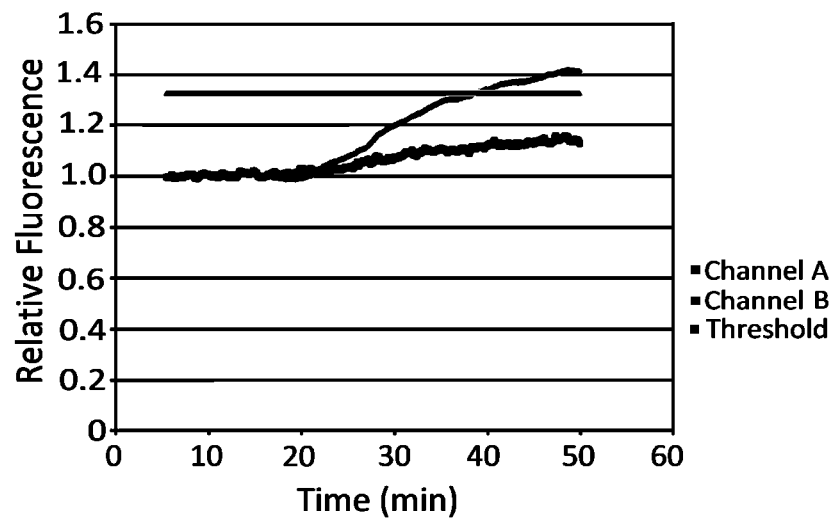
FIG. 13 is a graph showing results from NASBA analysis using the handheld detector for *Epinephelus morio*. The flat light grey line indicates a ratio of 1.3 from the baseline (initial) fluorescence, a benchmark we typically use to indicate the reaction is positive.
Figure 14:
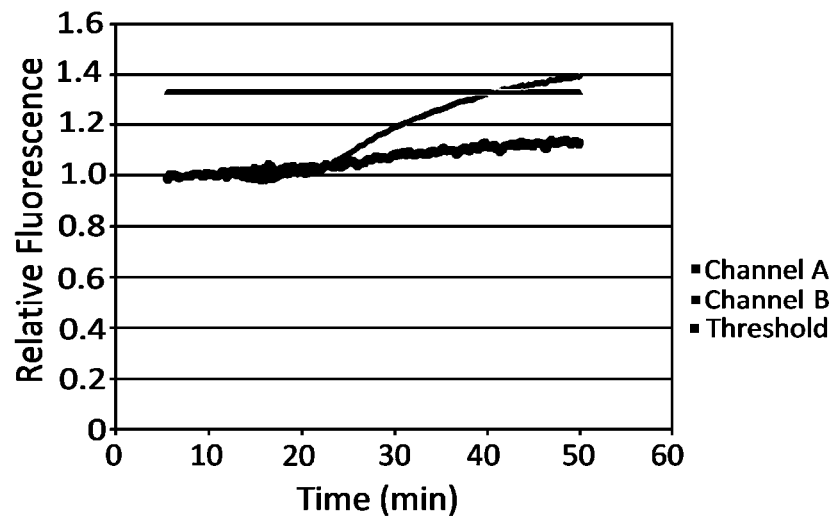
FIG. 14 is a graph showing results from NASBA analysis using the handheld detector for *Epinephelus diacanthus*. The flat light grey line indicates a ratio of 1.3 from the baseline (initial) fluorescence, a benchmark we typically use to indicate the reaction is positive.

Testing of Mycteroperca microlepis (gag grouper), Epinephelus morio (red grouper) and Epinephelus diacanthus (spiny cheek grouper) preps taken at the same time as those in Example 3 show that the detection procedure is effective in handheld detectors, as seen in FIGS. 12-14 versus the benchtop detection shown in FIGS. 3-11. A positive detection threshold ratio of 1.3 from baseline fluorescence was established for the handheld detector. As in the benchtop detection, the handheld detector showed time to positivity at around 35-40 minutes, slightly more than the NASBA system utilizing the benchtop detector.

Example 4

RNA was extracted from fish tissue using minute quantities of fish tissue samples and Zymo RNA extraction solutions using the field RNA extraction, as discussed above. A sample of E. diacanthus was prepared using RNA purification columns from two manufacturers: Zymo Research, which was a luer-lock syringe adapted column, and a Bio-Rad RNA purification column fitted with one of our custom syringe adapters. Both preparations employed Zymo buffers aliquoted into syringes as would be used in the field prep system. Briefly, the sample tissue was immersed in lysis buffer 30-60 seconds, with rigorous agitation. The buffer, containing liberated RNA, was transferred to the purification column (Zymo Mini RNA isolation II kit, Zymo Research Corp., Orange, Calif.) and a syringe used to pressurize the column and force the lysis buffer liquid through the column A series of buffers (Zymo Mini RNA isolation II kit) were run through the column, followed by 100% acetone, followed by a volume of water was used to elute the RNA from the column.

Figure 15:
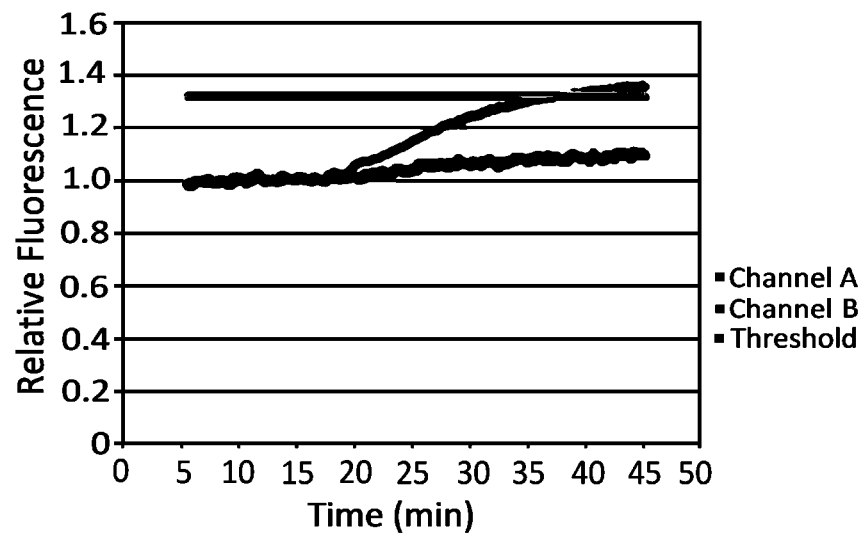
FIG. 15 is a graph showing the results of handheld trial using field-prep RNA extraction techniques using Zymo columns adapted to accept syringe air input. The Zymo columns amplified as efficiently as Bio-Rad RNA purification columns.
Figure 16:
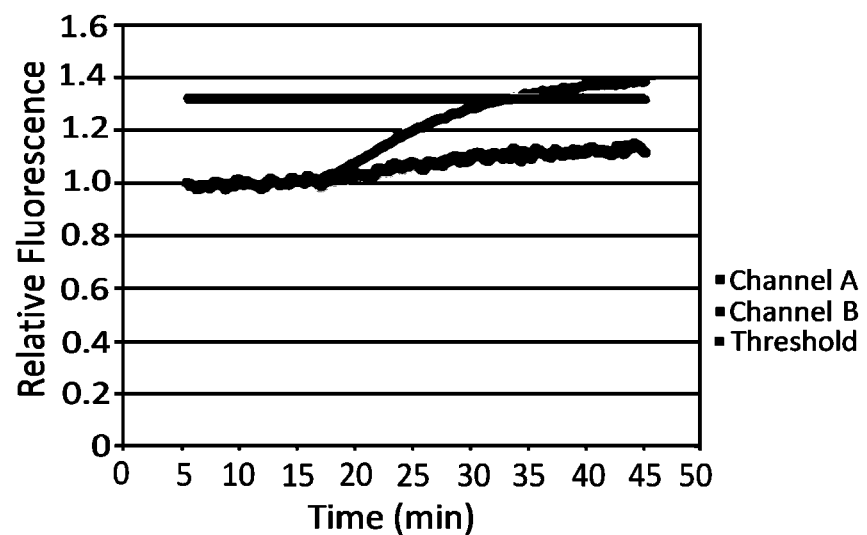
FIG. 16 is a graph showing the results of handheld trial using field-prep RNA extraction techniques using Bio-Rad RNA purification column and custom syringe adapter. The Bio-Rad RNA purification columns amplified as efficiently as the Zymo columns.
Figure 17:
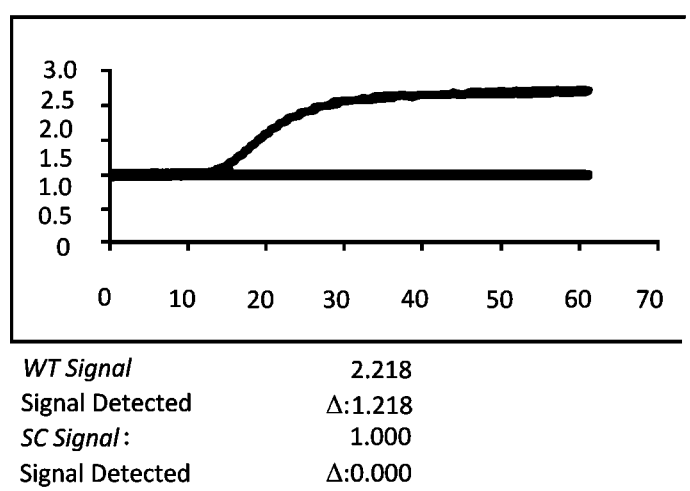
FIG. 17 is a graph showing the results of handheld trial using field-prep RNA extraction techniques. The Zymo column-prepared RNA was amplified and read on the EasyQ machine.
Figure 18:
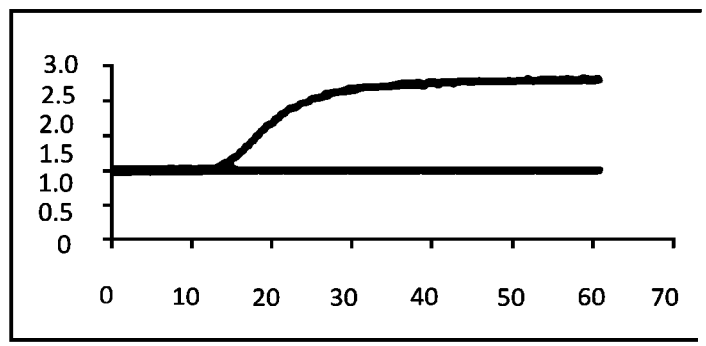
FIG. 18 is a graph showing the results of handheld trial using field-prep RNA extraction techniques. The Bio-Rad column-prepared RNA was amplified and read on the EasyQ machine.
Figure 19:
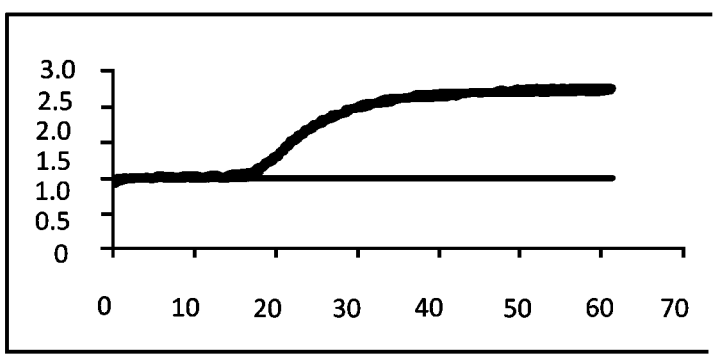
FIG. 19 is a graph showing the results of handheld trial using field-prep RNA extraction techniques. A positive control comprising in vitro transcript of *M. microlepis* 16S rRNA cloned gene were amplified and read on the EasyQ machine.

The resultant RNA was amplified using NASBA, in either a handheld detector as discussed in Example 3, or a benchtop detector as discussed in Examples 1 and 2. The use of Zymo Research purification columns, seen in FIG. 15, and Bio-Rad purification columns, seen in FIG. 16, were both effectively isolated RNA for use in the NASBA detection. Moreover, the handheld detector accurately determined whether the sample was grouper within about 35-40 minutes, compared to about 30 minutes for benchtop detectors, seen in FIGS. 17-19. The results support the use of field RNA extraction to effectively isolate RNA, and handheld detection systems.

Example 5

A field adaptation of the RNA extraction protocol (Casper et al., A handheld NASBA analyzer for the field detection and quantification of *Karenia brevis*. Harmful Algae. 2007; 6: 112-118; Paul, et al., In Situ Instrumentation. Oceanography. 2007; 20: 70-78) and materials is utilized to collect RNA for the NASBA. A tissue extractor, such as a biopsy punch, is used to extract a small (~5 mg) sample of fish tissue. The sample is extruded into a lysis buffer tube and fully immersed in lysis buffer (Zymo RNA extraction kit) for up to 10 minutes. Air pressure is used to force the lysis buffer liquid through an RNA extraction column (Zymo RNA extraction kit). A series of buffers preloaded into syringes, were run through the column, followed by 100% acetone, and the RNA eluted using a volume of water. The kit includes the appropriate disposable tubes and liquid transfer implements, aliquotted reagents, purification columns, and air-purging components to pass liquid and dry columns.

The system optionally employs re-constituted NASBA primers and beacons (oligonucleotides), which are stored in frozen liquid state or lyophilized in single-reaction size spheres, as discussed in Paul, et al. (Paul, et al., In Situ Instrumentation. Oceanography. 2007; 20: 70-78). Optional additional oligonucleotides (primers and beacons) are added to cover additional species and/or specifically detect undesired substitutes. The optional oligionucleotides and molecular beacons are multiplexed into combined reactions. Since identification of the individual species is not intended, confirmation as one of the grouper with a single positive reaction is possible. An internal control component is also optionally included, which is a molecule engineered to be identical to the target RNA except for a unique beacon binding site (Patterson et al. Increased precision of microbial RNA quantification using NASBA with an internal control. Journal of Microbiological Methods. 2005; 60: 343-352). A second molecular beacon is then used which fluoresces at a different wavelength such that amplification can be followed of both the target and the IC simultaneously. The IC can thus signal if a reaction is a false-negative. The assay may employ more than one reaction per sample to accommodate all combinations of species, using the multi-sample handheld analyzer.

The NASBA reaction spheres are pre-loaded into one or more reaction tubes for analysis of each sample. RNA extracted using the field-extraction kit is added to the set of reaction tubes and analyzed on the handheld analyzer (Bioplex SE-100). The handheld detector provides on-site, deployable NASBA fluorescence detectors (Farmer et al. A Hand-Held Thermal Regulating Fluorometer. Review of Scientific Instruments. 2005; 76: 115102), with additive modules that can be linked together to create a configurable multi-reaction platform. The next generation multiplexed (i.e. multiple-sample) heat regulated fluorometer is at this time in the prototype testing phase. The final multiplexed system utilizes 3D flexible systems packaging to enable a compact 3-dimensional folded flex multiplexed system. Additional reactor units can be appended to the right of the single block to enable up to eight units and achieve the multiplexed system with just one motherboard. The various subsystems of thermal, electrical, optical mechanical and systems layout have all been designed, built and tested.

Detection of amplified target and IC-RNA occurs through the use of a two-channel system. High intensity light emitting diodes (LEDs) are used as the fluorescence excitation light source with peak emissions at 470 nm and 550 nm. Fluorescence emissions are detected using blue-enhanced integrating photodiodes. To prevent unwanted LED excitation light from scattering into the emission photodetectors, both LEDs and photodiodes are optically isolated at 90° with 9×9 mm Omega Optical Inc. bandpass filters. Also, only the light source and photodetector pair associated with a fluorophore is active while detecting that particular fluorophore. This helps reducing the crossover detection between the two different fluorophores used in the reaction. The heater (R4) is a resistive heater made by etching the copper film on a flexible LCP (Liquid Crystal Polymer) substrate to a desired thickness and length to achieve a predetermined resistance value. A microcontroller controls the amount of heat generated in the heater by varying the duty cycle of its Pulse Width Modulated (PWM) signal. The resistive heater also substitutes as a temperature detector; PWM output generated by the microcontroller is periodically turned off to measure the voltage across the heater, which represents the resistance value of the heater at a particular temperature. The temperature inside the reaction block is thus maintained at a desired temperature, 41° C. (+/−0.5).

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of methods for the detection of grouper meat, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of detecting whether seafood originates from a grouper species, comprising:
    collecting a sample of muscle from a fish;
    extracting RNA from the fish muscle;
    amplifying the RNA using nucleic acid sequence based amplification, wherein the nucleic acid sequence based amplification uses a forward primer and a reverse primer designed to specifically amplify a region of 16S rRNA of a grouper species;
        wherein the forward primer and the reverse primer are compatible with nucleic acid sequence based amplification;
    adding a molecular probe to the nucleic acid sequence based amplification reaction, wherein the molecular probe is SEQ ID NO: 7 and fluoresces when hybridized to a target molecule;
    hybridizing the molecular probe with the amplified RNA; and
    detecting that the seafood originates from a grouper species when the fluorescence from the molecular probe hybridized to the amplified RNA product is detected.

2. The method of claim 1, wherein the RNA is extracted by
    immersing the collected sample muscle in lysis buffer for 30 seconds to 10 minutes to form a lysis solution;
    adding the lysis solution to a RNA purification column;
    removing liquid from the lysis solution using pressurized air to form a lysis product;
    washing the lysis product with at least acetone or ethyl alcohol; and
    eluting the RNA using water.

3. The method of claim 1, wherein the forward primer is SEQ ID NO: 1 or SEQ NO: ID 4.

4. The method of claim 1, wherein the reverse primer is SEQ ID NO 2 or SEQ ID NO: 5.

5. The method of claim 1, further comprising adding additional molecular probes designed to bind to and detect a non-grouper species of fish, designed not to bind to any species of fish, designed to bind to a control sequence, or a combination thereof.

6. The method of claim 5, further comprising comparing the signal generated from hybridization of the molecular probe to a control sequence against the signal generated from hybridization of the molecular probe to the amplified RNA collected from the fish muscle, wherein the ratio is indicative of positive detection of the grouper species.

7. The method of claim 1, wherein the fluorescence is evaluated based upon a threshold value ratio of 1.34 or 1.3 fluorescence from the amplified RNA-hybridized molecular probe to a baseline fluorescence level.

8. The method of claim 1, further comprising adding at least one additional molecular probe to the nucleic acid sequence based amplification reaction, wherein the at least one additional molecular probe is SEQ ID NO: 3, SEQ ID NO: 6, or a combination thereof.

9. A method of detecting whether an unknown seafood is a grouper species, comprising:
    collecting a sample of muscle from a fish;
    extracting RNA from the fish muscle;
    amplifying the RNA using nucleic acid sequence based amplification, wherein the nucleic acid sequence based amplification uses a forward primer selected from the group consisting of SEQ ID NO: 1 and SEQ ID NO: 4, and a reverse primer selected from the group consisting of and SEQ ID NO: 2 and SEQ ID NO: 5;
    adding a molecular beacon probe to the nucleic acid sequence based amplification reaction, wherein the molecular beacon probe is SEQ ID NO: 7;
    hybridizing the molecular beacon probe with the amplified RNA; and
    detecting that the seafood originates from a grouper species when the fluorescence from the molecular beacon probe hybridized to the amplified RNA product is detected.

10. The method of claim 9, wherein the RNA is extracted by
    immersing the collected sample muscle in lysis buffer for 30 seconds to 10 minutes to form a lysis solution;
    adding the lysis solution to a RNA purification column;
    removing liquid from the lysis solution using pressurized air to form a lysis product;
    washing the lysis product with at least acetone or ethyl alcohol; and
    eluting the RNA using water.

11. The method of claim 9, further comprising adding additional molecular beacon probes designed to bind to and detect a non-grouper species of fish, designed not to bind to any species of fish, designed to bind to a control sequence, or a combination thereof.

12. The method of claim 11, further comprising comparing the signal generated from hybridization of the molecular beacon probe to a control sequence against the signal generated from hybridization of the molecular beacon probe to the amplified RNA collected from the fish muscle, wherein the ratio is indicative of positive detection of the grouper species.

13. The method of claim 9, wherein the fluorescence is evaluated based upon a threshold value ratio of 1.34 or 1.3 fluorescence from the amplified RNA-hybridized molecular beacon probe to a baseline fluorescence level.

14. The method of claim 9, further comprising adding at least one additional molecular probe to the nucleic acid sequence based amplification reaction, wherein the at least one additional molecular probe is SEQ ID NO: 3, SEQ ID NO: 6, or a combination thereof.

* * * * *